Figure 1:
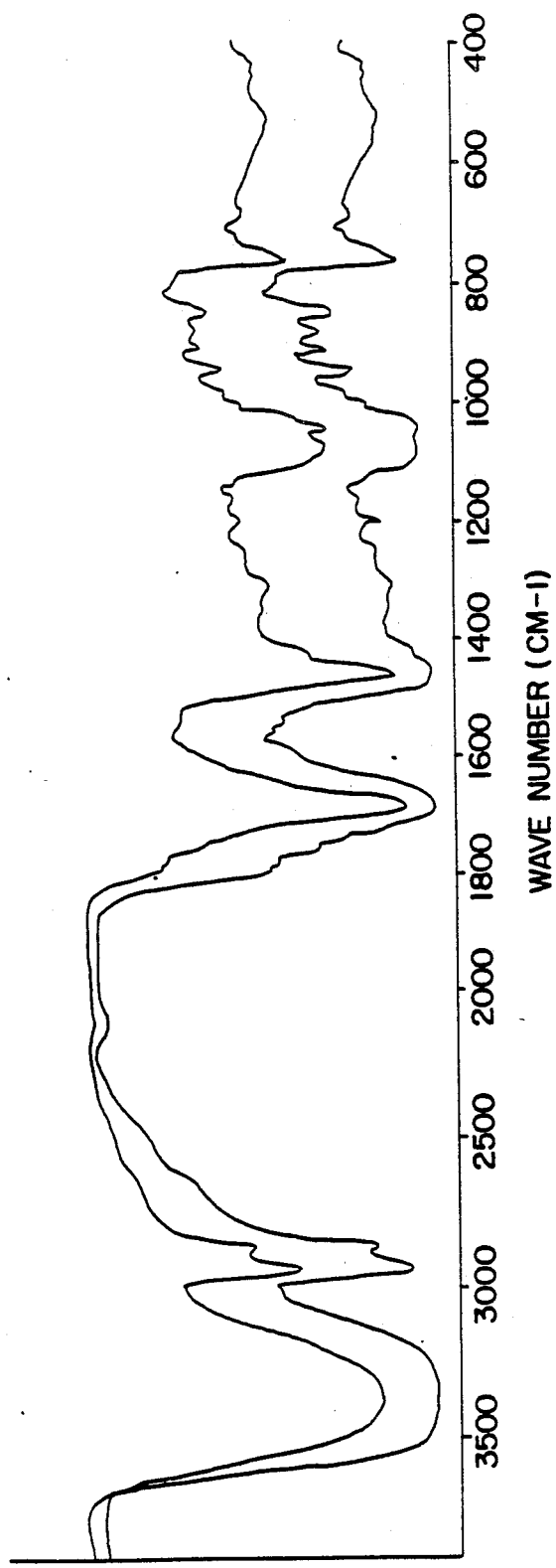

United States Patent [19]

Teissier et al.

[11] Patent Number: 4,874,859
[45] Date of Patent: Oct. 17, 1989

[54] DI-BISHYDROXYPROPYL CYANURIC ACID, TRISUBSTITUTED DERIVATIVES THEREOF AND A PROCESS FOR THEIR PREPARATION

[75] Inventors: Remy Teissier, Toulouse; Serge Clamens, Tournefeuille, both of France

[73] Assignee: Societe Chimique des Charbonnages, Paris, France

[21] Appl. No.: 131,793

[22] Filed: Dec. 11, 1987

[30] Foreign Application Priority Data

Dec. 11, 1986 [FR] France ................. 86 17329

[51] Int. Cl.$^4$ ............... C07D 251/04; C08F 20/00; C08F 283/04; C08G 18/10
[52] U.S. Cl. ........................... 544/221; 525/440; 525/454; 525/455; 528/59; 528/75; 528/76; 528/80
[58] Field of Search .......................... 544/221

[56] References Cited

U.S. PATENT DOCUMENTS 4,020,087 4/1977 Hiestand et al. ................ 544/215

FOREIGN PATENT DOCUMENTS 2060633 5/1981 United Kingdom ............. 544/215

OTHER PUBLICATIONS

Chemical Abstracts, vol. 85, No. 18, Nov. 1, 1976, p. 52, No. 125199a.
Chemical Abstracts, vol. 101, No. 2, Jul. 9, 1984, pp. 36–47, No. 81869.

Primary Examiner—Mary C. Lee
Assistant Examiner—J. Richter
Attorney, Agent, or Firm—Millen, White & Zelano

[57] ABSTRACT

The subject of the invention is new derivatives (I) and (II) of cyanuric acid which have the formula, respectively,

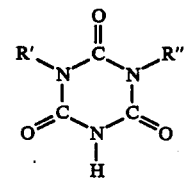

and

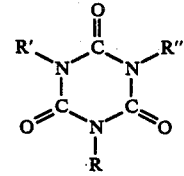

in which:
R' and R" are —CH$_2$—CH(OH)—CH$_2$OH and
R is an alkyl containing a polymerizable ethylenic functional group such as an acrylic, methacrylic or allyl group.

The derivatives (I) and (II) according to the invention may be employed as crosslinking agents in polymers.

4 Claims, 2 Drawing Sheets

WAVE NUMBER (CM-1)

DI-BISHYDROXYPROPYL CYANURIC ACID, TRISUBSTITUTED DERIVATIVES THEREOF AND A PROCESS FOR THEIR PREPARATION

CROSS-REFERENCE TO RELATED APPLICATIONS

This application is related to our application entitled "DICHLOROHYDRINS OF CYANURIC ACID, TRISUBSTITUTED DERIVATIVES THEREOF AND A PROCESS FOR THEIR PREPARATION", based on French Application Ser. No. 86/17329, filed Dec. 11, 1986 [Attorney's Docket No. CDF 63], this application being incorporated by reference herein.

The present invention relates to new derivatives of cyanuric acid which are 1,3-bis(dihydroxypropyl) isocyanurate, trisubstituted derivatives of cyanuric acid, and a process for their manufacture.

Many organic derivatives of cyanuric acid are known. These are triazine derivatives substituted on nitrogen of formula:

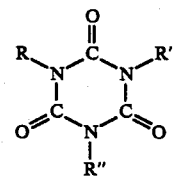

Among the known derivatives of cyanuric acid there may be mentioned 1,3,5-tri(3-chloro-2-hydroxypropyl) isocyanurate in which

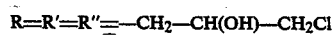

$R = R' = R'' = -CH_2-CH(OH)-CH_2Cl$

This derivative may be employed as a reaction intermediate in the preparation of triglycidyl isocyanurate. It may be obtained by the reaction of cyanuric acid, formalin and epichlorohydrin (Polish Patent No. 99,060/1975).

Triallyl isocyanurate, in which R, R' and R'' are $CH_2=CH-CH_2-$ radicals is also known. It is prepared by the reaction of allyl chloride with tri-sodium cyanurate. It is employed as a crosslinking agent, especially in polyesters.

Nitrogen-trisubstituted derivatives of cyanuric acid, in which the radicals R, R' and R'' are different are also known. Among these there may be mentioned diallyl monacryloyloxyethyl isocyanurate, in which:

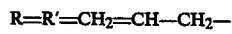

$R=R'=CH_2=CH-CH_2-$ and $R''=CH_2=CH-C(O)-O-CH_2-CH_2-$

These derivatives are described particularly in French Patent No. 2,560,874. They may be polymerized or copolymerized with acrylic monomers or may also be employed as a crosslinking agent in polymers such as polyethylenes and polystyrenes. They impart fire-resistant properties to the latter.

The first subject of the present invention is a new derivative (I) of cyanuric acid which is 1,3-bis(dihydroxypropyl) isocyanurate and is of formula:

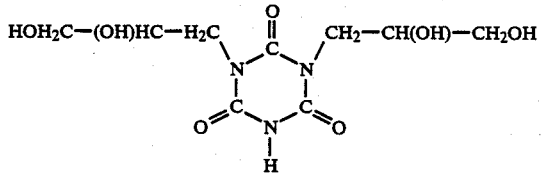

The infrared spectrum (FIG. 1) and the $^{13}C$ carbon magnetic resonance ($^{13}C(NMR)$) spectrum (FIG. 2) confirm the structure of the derivative (I), namely 1,3-bis(dihydroxypropyl)-1,3,5-(1H,3H,5H)triazine-2,4,6-trione or 1,3-bis(dihydroxypropyl)isocyanurate. Its empirical formula is $C_9H_{15}N_3O_7$. Its molecular weight is 277.35. At ambient temperature it is a highly viscous and hygroscopic whitish material. It is soluble in water and in alcohols such as methanol, ethanol and propanol. On the other hand, it is insoluble in acetone, in aromatic solvents, and in ether. 1,3-Bis(dihydroxypropyl) isocyanurate (I) may be prepared in various ways. For example, it may be obtained from 1,3-di(chlorohydroxypropyl) isocyanurate by an alkaline hydrolysis reaction. A reaction medium with a pH of at least 10, preferably at least 11, obtained, for example, with the aid of aqueous sodium hydroxide or potassium hydroxide is preferably employed. The molar ratio of the basic functional groups $OH^{(-)}$ to di(chlorohydroxypropyl) isocyanurate is at least 3.

The temperature of the reaction mixture is preferably between the ambient and 50° C. in order to avoid the hydrolysis reaction of the cyanuric ring.

At the end of reaction, 1,3-bis(dihydroxypropyl) isocyanurate is recovered by extraction with epichlorohydrin, ethanol or acetonitrile.

The second subject of the present invention is the trisubstituted derivatives (II) of cyanuric acid which may be obtained from 1,3-bis(dihydroxypropyl) isocyanurate and which have the formula:

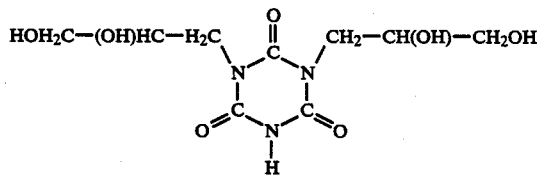

in which R is an alkyl group containing a polymerizable ethylenic functional group such as an acrylic, methacrylic or allyl group.

The derivatives (II) according to the invention are generally colourless viscous materials which crystallize at low temperature, at about −30° C.

The products (II) according to the invention, as well as 1,3-bis(dihydroxypropyl) isocyanurate, may be employed as crosslinking agents in polymers such as polyolefins, polyacrylics, polystyrenes, polyallyl derivatives and polycondensates such as polyesters and epoxides.

They impart properties such as good resistance to heat and to UV radiations to these polymers.

Furthermore, they make these polymers water-soluble.

The products (II) may also be polymerized or copolymerized with monomers such as (meth)acrylic monomers, allyl monomers, and ethylenic monomers such as ethylene, propylene, vinyl chloride and styrene.

The use of various methods may be considered for the preparation of the trisubstituted derivatives (II) according to the invention. The trisubstituted derivatives (II) may be prepared by reacting 1,3-bis(dihydroxypropyl) isocyanurate with a halide RX, X being a halogen and R being an alkyl group containing a polymerizable ethylenic functional group such as an acrylic, methacrylic or allyl group. The reaction is carried out in the presence of at least one catalyst of the phase transfer type, for example quaternary ammoniums, at a temperature of between 50° and 140° C.

The reaction is generally performed at a temperature of between 50° and 100° C. It is preferably conducted at the reflux temperature of the halide or that of water in the case where the boiling point of the halide is higher than 100° C. The reaction may also be carried out at a temperature between 100° and 140° C., but in an autoclave. The derivatives (II) according to the invention decompose above 140° C., and the reaction kinetics are very slow at a temperature below 50° C.

When the reaction has ended, the trisubstituted derivative (II) obtained is isolated and purified by extraction with a solvent such as acetone.

A molar ratio of 1,3-bis(dihydroxypropyl) isocyanurate to the halide which is equal to 1 or slightly lower is preferably employed so as to have the advantage of a slight excess of halide.

Also preferably, the reaction is carried out with concentrations of 1,3-bis(dihydroxypropyl) isocyanurate and of halide in water which do not exceed 0.5 mole/liter, in order to have a reaction mixture of low viscosity.

Among the alkyl halides which may be employed in the process according to the invention there may be mentioned chloroethyl acrylate, chloromethyl acrylate, chloroethyl methacrylate and chloromethyl methacrylate.

Among the catalysts which may be employed in the process according to the invention there may be mentioned, for example, tetraethylammonium chloride, tetraethylammonium bromide, tetraethylbenzylammonium chloride, tetraethylbenzylammonium bromide, tertiary amines such as trimethylamine or triethylamine, or quaternary phosphonium salts such as, for example, methylphenylphosphonium bromide. The catalyst is preferably employed in a molar ratio of between $10^{-2}$ and $10^{-1}$ relative to 1,3-di(chlorohydroxypropyl) isocyanurate.

EXAMPLE 1

Preparation of 1,3-bis(dihydroxypropyl) isocyanurate

After trichlorocyanuric acid has been reacted with diallyl isocyanurate, the cyanuric acid liberated is filtered off. 62.5 g of 96% NaOH pellets (3/2 moles) are added with stirring, to the clear aqueous solution containing 0.5 mole (157 g) of 1,3 di(chlorohydroxypropyl) isocyanurate. The temperature rises to a maximum of 35° C. chiefly because of the dissolution of the sodium hydroxide. The solution is left stirred for at least 16 hours. After 24 hours, 95% of the stoichiometric quantity (1 mole) of sodium hydroxide has been consumed, while 98% of the stoichiometric quantity of NaCl has appeared (acidimetric determination - determination of Cl$^{(-)}$ by silver determination). The temperature of the reaction mixture has then fallen to the ambient (time t=reference employed in Examples 4 and 5 which follow). After neutralization to pH 4, the mixture is concentrated under vacuum down to approximately 0.5 liter. 0.5 to 1 liter of acetone is added. A viscous whitish deposit appears and is separated off by centrifuging. This deposit (called product A hereinafter) is taken up with epichlorohydrin. The NaCl precipitated by the acetone at the same time as 1,3-bis(dihydroxypropyl) isocyanurate is filtered off. 58.5 g of a very hygroscopic, translucent viscous product are recovered. 55 g of 1,3-bis(dihydroxypropyl) isocyanurate have thus been recovered, i.e. 40% yield based on diallyl isocyanurate. Quantitative analysis by silver determination shows that there is about 6% of NaCl in the product, which is confirmed by the following elemental analysis:

|   | Measured | Normalized to 100% | Theoretical |
|---|---|---|---|
| C | 36.54% | 38.64% | 38.91% |
| H | 5.5% | 5.82% | 5.42% |
| N | 14.00% | 14.81% | 15.16% |
| O | 38.52% | 40.73% | 40.43% |
| Total | 94.56% | 100% | 100% |

The NMR spectrum (FIG. 2) and the infrared spectrum (FIG. 1) confirm the structure of the product. In the infrared spectrum (FIG. 1):

Broad band between 3500 and 3200 cm$^{-1}$ corresponds to OH and NH

Peaks at 2940 cm$^{-1}$ and 2860 cm$^{-1}$ correspond to CH$_2$

Peaks at 1770 cm$^{-1}$ correspond to CO

Peaks at 1460 cm$^{-1}$ correspond to the cyanuric ring

Bands at about 1100 cm$^{-1}$ correspond to C-OH and to glycols

Band at 760 cm$^{-1}$ corresponds to the cyanuric ring.

EXAMPLE 2

Preparation of 1,3-bis(dihydroxypropyl) isocyanurate

Figure 2:
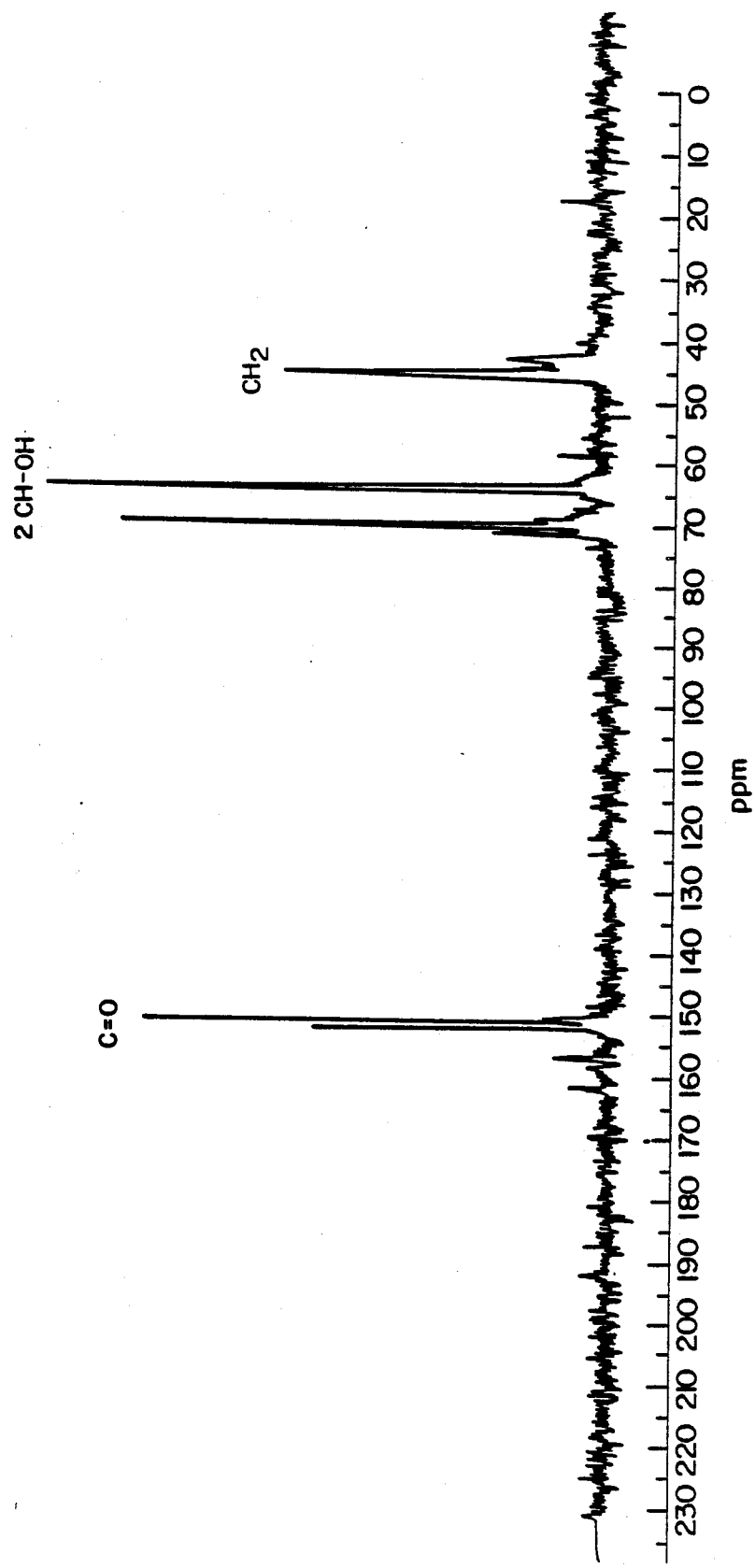

The product (A) obtained in Example 1 is taken up with absolute ethanol, which is evaporated off. 165 g of a viscous product containing approximately 34% of NaCl are recovered. The infrared spectrum is identical with that obtained in Example 1 (FIG. 1). In this mixture there are 110 g of bis(dihydroxypropyl) isocyanurate, i.e. 80% yield based on diallyl isocyanurate.

A second extraction with ethanol produces 96 g of a product which contains 10.6% of NaCl, that is to say a yield of 61% based on diallyl isocyanurate.

EXAMPLE 3

Preparation of 1,3-bis(dihydroxypropyl) isocyanurate

The extraction of product (A) is carried out using methanol. After 3 extractions, 103 g of a hygroscopic viscous product are obtained; this contains approximately 15% of NaCl and has an infrared spectrum which is identical with those preceding (refer to FIG. 1).

EXAMPLE 4

Preparation of 1,3-bis(dihydroxypropyl) 5-monoallyl isocyanurate

In order to prepare this compound, the reaction mixture prepared in Example 1 is employed unpurified and unneutralized and such as obtained at time t, referred to in that example. To this reaction mixture are added:

39 g of allyl chloride (0.51 mole)

5 g of a product of trade name Triton B (aqueous solution containing 40% of benzyltrimethylammonium hydroxide).

The mixture is heated to reflux, which begins at about 48° C. As the allyl chloride reacts, the reflux temperature rises. After 4 hours it stabilizes at about 95.6° C. Cooling is applied. The chloride ions are determined by silver determination. Approximately 0.45 mole of $Cl^{(-)}$ has appeared during this reaction, i.e. a reaction conversion of 90%. The material is concentrated under vacuum. A paste is obtained and is extracted 3 times with acetone. The acetone is evaporated off. 602 g of 1,3-bis(-dihydroxypropyl) 5-allyl isocyanurate are obtained as a viscous product (yield based on the diallyl compound: 38%).

The additional analysis confirms the product:
C : 44.82% (th 45.43%
H : 6.14% (th 5.99%)
N : 12.95% (th 13.25%)
O : 35.87% (th 35.33%)

This product is soluble in water, in alcohols and in acetone. It is insoluble in ether and in aromatics.

EXAMPLE 5

Preparation of 1,3-bis(dihydroxypropyl) 5-monobenzyl isocyanurate

For the preparation of this compound, the reaction mixture prepared in Example 1 is employed unpurified and unneutralized and such as obtained at time t referred to in that example. To this reaction mixture, which contains 0.5 mole of bis(dihydroxypropyl) isocyanurate, are added:

65 g of benzyl chloride (0.51 mole)
5 g of a product of trade name Triton B.

The reaction mixture is heated under reflux for at least 6 hours (reflux temperature 100° C.). After 6 hours cooling is applied. The reaction conversion is assessed at 84% by determination of the chloride ions. The product is concentrated under vacuum. The product is extracted with acetone from the paste obtained. The acetone is evaporated off. 66 g of a viscous white product which crystallizes slowly are obtained. This may be recrystallized from hot acetone and 54 g of a crystalline white product are then obtained (the yield based on diallyl isocyanurate is 29.5%). The elemental analysis confirms the product:

C: 51.86% (th 52.32%)
H: 6.04% (th 5.72%)
N: 11.12% (th 11.44%)
O: 31.23% (th 30.52%)

We claim:

1. A trisubstituted derivative of cyanuric acid of the formula (II)

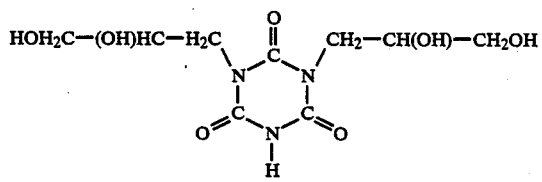

wherein R is an alkyl group containing a polymerizable ehtylenic functional group.

2. A derivative of claim 1, wherein R is an acrylic methacrylic or allyl group.
3. A derivative of claim 2, wherein R is monoallyl.
4. A cyanuric acid derivative of the formula (I)

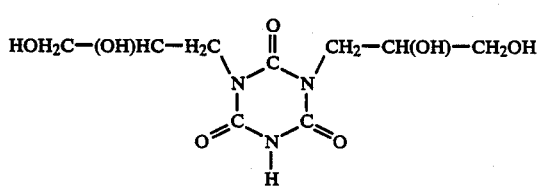

* * * * *